United States Patent [19]

Kruse

[11] 4,120,824

[45] Oct. 17, 1978

[54] TETRAVALENT MANGANESE-CARBON OXIDATION CATALYSTS AND METHODS OF THEIR PREPARATION

[75] Inventor: Walter M. Kruse, Wilmington, Del.

[73] Assignee: ICI Americas Inc., Wilmington, Del.

[21] Appl. No.: 788,138

[22] Filed: Apr. 18, 1977

[51] Int. Cl.$^2$ .................. B01J 21/18; B01J 23/34; C08G 61/10; C07C 37/00

[52] U.S. Cl. .................. 252/447; 260/396 N; 260/580; 260/596; 260/599; 260/603 C; 260/613 R; 260/647; 528/568; 528/730; 528/219; 528/729; 528/723

[58] Field of Search .............. 252/447, 444, 422, 471

[56] References Cited

U.S. PATENT DOCUMENTS

| | | | |
|---|---|---|---|
| 2,055,475 | 9/1936 | Sidney | 252/447 |
| 3,434,479 | 3/1969 | Till | 252/471 |
| 3,541,025 | 11/1970 | Oda et al. | 252/421 |
| 3,700,605 | 10/1972 | Dodman et al. | 252/447 |
| 3,884,830 | 5/1975 | Grant | 252/444 |

FOREIGN PATENT DOCUMENTS 1,329,505  5/1963  France ................ 252/444

OTHER PUBLICATIONS

*Journal of Organic Chemistry*, vol. 35, No. 4 (1970), "Simple Prep. of Active Manganese Dioxide from Activated Carbon;" Carpino, L. A.

*Primary Examiner*—P. E. Konopka
*Attorney, Agent, or Firm*—H. Jolyon Lammers

[57] ABSTRACT

Tetravalent manganese precipitated on porous carbon provide useful oxidation catalysts. They may be prepared by slurrying potassium permanganate and porous carbon under alkaline conditions.

7 Claims, No Drawings

TETRAVALENT MANGANESE-CARBON OXIDATION CATALYSTS AND METHODS OF THEIR PREPARATION

DESCRIPTION OF THE PRIOR ART

Oxidation catalysts containing oxides of manganese are well known in the art. Catalysts containing oxides of manganese supported on granular alumina were disclosed in U.S. Pat. No. 1,995,274 assigned to Carbide and Carbon Chemicals Corporation. The oxidative coupling of phenols in the presence of a catalyst containing manganese has also been known. For example U.S. Pat. No. 3,825,521 assigned to Asahi-Dow Ltd. suggests the coupling of 2,6-disubstituted phenols in the presence of homogeneous chelate type catalyst comprising at least one divalent manganese salt and at least one selected diamino compound. U.S. Pat. No. 3,300,536 issued to McNelis and assigned to Sun Oil Company discloses a method of coupling 2-naphthol in the presence of a stoichiometric amount activated manganese dioxide. U.S. Pat. No. 3,787,361 assigned to Sumitomo Chemical Limited suggests a process for the production of polyphenylene oxide compounds by polymerizing phenols in the presence of a homogeneous catalyst system composed of a manganese compound, a primary amine and an alcohol. A tetravalent manganese on carbon catalyst composition comprising 30 percent by weight manganese is disclosed by Louis A. Carpino in the Journal of Organic Chemistry, Vol. 35, No. 4, (1970). None of the prior art however suggests a heterogeneous catalyst composition consisting essentially of 1 to 10 percent by weight of tetravalent manganese precipitated on porous carbon.

SUMMARY OF THE INVENTION

In accordance with the present invention there is provided a heterogeneous catalyst composition consisting essentially of about 1 to 10 percent by weight of tetravalent manganese precipitated on porous carbon.

The catalysts compositions useful in the present invention consist essentially of about 1 to 10 percent by weight of tetravalent manganese precipitated on porous carbon. The catalysts are unusually active and have a molecular oxygen consumption factor of at least 4.5 as determined by the molecular oxygen consumption test described hereinafter.

Carbons which are useful in the preparation of the catalysts have a surface area of at least 500 m$^2$/grams and include those prepared from wood or wood products such as sawdust as well as from coconut shells, lignite, or coal. Catalysts prepared from lignite require a preparative acid wash to substantially remove the sulfur and metal oxide impurities. In general the carbons that are suitable are those carbons which are prepared by pyrolysis, oxidation, steam extraction or acid extraction. Carbons such as most channel blacks possess a porosity and surface area insufficient for the purpose of this invention. Useful carbons are commercially available and include Darco G-60 activated carbon and similar carbons which are prepared from pine wood stumps and other carbohydrate or saccharide sources, Darco KB activated carbon which is prepared from sawdust by a phosphoric acid process, Darco S-51 and Darco M activated carbons which is prepared from lignite by steam activation followed by an acid wash. It is highly desirable to remove any mineral impurities such as phosphates, sulfates or metal oxides in the carbon prior to using the carbon in the formation of the catalysts to avoid inter-reaction between the manganese component and these impurities. All Darco brand activated carbons are available from ICI United States Inc.

The tetravalent manganese/carbon catalyst having utility in the invention may be prepared by slurrying an aqueous permanganate salt solution such as potassium permanganate with a suitable carbon. In the case of sodium or potassium permanganate it has been observed that the purple color of the solution disappears during slurrying which indicates a valance reduction of the manganese $^{VII}$. Suitable permanganate salts include lithium permanganate, potassium permanganate, sodium permanganate, cesium permanganate and rubidium permanganate. Preferred permanganates are those which are substantially soluble in water. Less soluble permanganates salts which therefore would be less preferred include cesium permanganate and rubidium permanganate. After the permanganate solution has been slurried with the carbon the resulting catalyst is washed, dried at temperatures below 25° C. and is then ready for use. It is highly desirable to dry the catalyst by vacuum drying or freeze drying as opposed to oven drying since high temperatures which prevail during oven drying tend to diminish the activity of the catalyst. For similar reasons it is suggested that the catalyst be kept in a cool dry environment prior to use. Catalyst kept at room temperature retain activity for approximately two months. Catalyst stored at lower temperatures retain activity for as long as six months.

The amount of manganese present in the total catalyst compositions may vary within the range of 1 to 10 percent by weight. For obvious economic reasons it is preferred to use as little manganese as possible. It has been discovered that a range of 1 to 10 percent of manganese precipitated on carbon provides a highly active catalyst. Percentages larger than 10 percent of manganese besides being economically disadvantageous also result in compositions with reduced activity. An optimum content of 2 to 7% manganese by weight of catalyst composition has been discovered to be most preferred for most oxidation reactions. Catalyst containing less manganese component but within the suggested range require larger amount of catalyst to achieve an optimum oxidative polymerization reaction.

The valence state of the active manganese component on the carbon must be four and this valence may be determined by utilizing a photoelectron spectrometer such as Model E S-200 available from AEI Scientific Apparatus Limited. Analyses of catalysts prepared for use in the process of the invention indicate that the active manganese is present only as tetravalent manganese. Total manganese content may be determined by atomic absorption analysis.

The catalysts of the invention are particularly useful in oxidation reactions. Specifically the catalysts are useful in the oxidation of polyols and sugars and the oxidative coupling of alkyl phenols. Other uses include the oxidation of phenyl hydrazides to carboxylic acids; the oxidation of primary alcohols to aldehydes, such as benzyl alcohol to benzaldehyde; the oxidation of secondary alcohols to ketones, such as 4-hydroxy-3-hexanone to 3,4-hexanedione; and the oxidation of hydroxyamines to nitroso compounds.

In order to describe the present invention so that it may be more clearly understood, the following examples are set forth. These examples are given primarily for the purpose of illustration and any enumeration of detail contained therein should not be interpreted as a limitation on the concept of the present invention.

MOLECULAR OXYGEN CONSUMPTION FACTOR (MOCF)

The MOCF represents the amount of oxygen consumed in two hours in a specific oxidation reaction. The amount is expressed in millimoles of molecular oxygen. The reaction conditions are as follows: a 50 ml flask held in a semi-automatic shaker apparatus is charged with:

2.44 grams (20 mmoles) 99.9% pure 2,6-xylenol,
20 ml of commercial grade tert-amyl alcohol,
0.10 grams of 85% powdered potassium hydroxide, and an amount of catalyst representing 0.025 grams of tetravalent manganese.

The reaction mixture is heated to 50° C. and allowed to consume oxygen at atmospheric pressure as required from a calibrated gas buret filled with oxygen. The amount of oxygen consumed in two hours is measured and represents the MOCF.

Catalyst Preparation

EXAMPLE 1

To 40 g of Darco G-60 Special activated carbon suspended in 400 ml of water was added over a 10 minute period 6.4 g of $KMnO_4$ dissolved in 200 ml of water. After one hour stirring at room temperature the color of $KMnO_4$ had disappeared and the pH of the reaction liquid was determined to be between 9–10 by pH test paper. After filtration and washing with 300 ml of water the material was dried in a vacuum oven for 2 hours at 40°–150° C. The catalyst contained 5.2% tetravalent manganese.

EXAMPLE 2

The procedure of example 1 was repeated using 1.3 g of $KMnO_4$. The catalyst contained 1% tetravalent manganese.

EXAMPLE 3

The procedure of example 2 was repeated using 3.2 g of $KMnO_4$. The catalyst contained 2.5% tetravalent manganese.

EXAMPLE 4

The procedure of example 1 was repeated using 12.8 g of $KMnO_4$. The catalyst contained 10% tetravalent manganese.

EXAMPLE 5

The procedure of example 1 was repeated but the material was "freeze dried" in a vacuum oven at room temperature.

EXAMPLE 6

The procedure of example 5 was repeated using 40 g of Darco KB Special activated carbon. The catalyst contained 5% tetravalent manganese.

EXAMPLE 7

The procedure of example 5 was repeated using 40 g of Darco S-51 activated carbon. The catalyst contained 5% tetravalent manganese.

EXAMPLE 8

The procedure of example 1 was repeated using Darco-M activated carbon. The catalyst contained 5% tetravalent manganese.

Catalyst Utility

EXAMPLE 9

A 500 ml reactor kettle equipped with stirrer, $N_2$ sparge system and oxygen inlet was charged with 65 ml of toluene and 0.75 ml of pyridine (9 mmole). After stirring under a nitrogen atmosphere 0.20 g of powdered 85% KoH was added followed by 24.4g of 99.9% 2,6-xylenol (200 mmol) and 15 ml of toluene. The mixture was stirred for 15 minutes after which 2.5g of a 5% manganese $^{IV}$ catalyst prepared according to Example 5 and 20 ml of toluene was added. The mixture was stirred for an additional half hour and then both stirrer and nitrogen were turned off. The reactor was flushed for ¼ hour at 20° with oxygen and then sealed. Oxygen supply was continued, the temperature allowed to rise up to 26°–30° and the mixture was stirred for the next 6 hours. The oxygen consumption was 95.5 mmoles of which 95 mmoles was consumed during the first 4 hours. After turning off the stirrer the reaction mixture was allowed to stand.

The viscous black product was diluted with 150 ml toluene, stirred and centrifuged. The clear yellow viscous toluene solution was decanted. The residue was stirred with 200 ml toluene, and centrifuged. The toluene solution was mixed with the original toluene centrifugate, evaporated to 150 ml, and poured into 400 ml stirred acetone. The resulting polymer weighed 4.8 grams (20 mole % yield). It melted 230°–260°. Gel permeation chromatography showed $M\bar{n}$ = 17,800; $M\bar{w}$ = 89,600; and polydispersity = 5.04.

The toluene-acetone solution was evaporated to dryness. The reddish yellow polymer weighed 1.6 gram and was low molecular weight oligomer of 2,6-xylenol (6.6% yield).

The catalyst-polymer solid residue from the toluene washes was air dried. The solid was stirred with 300 ml methylene chloride, centrifuged, and the methylene chloride solution was filtered through a thin pre-coat of Super-Cel filter aid. This operation was repeated once. The filtered methylene chloride solution was allowed to stand to precipitate the polymer-methylene chloride complex. The complex was removed by filtration. The methylene chloride was evaporated to dryness to yield 2.0 grams of red tetramethyldiphenoquinone (8.4 mole % yield).

The solid catalyst remaining after the methylene chloride extractions was stirred with 300 ml 1,1,2-trichloroethylene and centrifuged. This operation was repeated once. The polymer-methylene chloride complex was dissolved in the trichloroethylene centrifugate, and the solution filtered through Super-Cel filter aid. The filtrate was evaporated to 550 ml, and then dropped into 1900 ml stirred acetone. The precipitated polymer was removed by filtration, and was washed once with acetone. The polymer was dried at 60°. The dried polymer was white, and weighed 14.7 grams (61.5 mole % yield). The polymer softened at 250°, and was still only soft at 300°. GPC analysis showed $M\bar{n}$ = 30,900; $M\bar{w}$ = 156,000; polydispersity = 5.07. Total yield of high polymer was 81.5 mole % with average Mn = 27,700.

Example 9-23 illustrates the activity of the catalysts and the method of oxidative coupling of alkyl phenols. The Examples 10-23 were all conducted according to the procedure of Example 9 varying as indicated in the Table the amounts of alkaline material and the amounts and types of amine. Mixing orders were varied as indicated. All molecular weights were determined by gel permeation chromatography (GPC).

The high MW polymers were cast into films by the following technique. The polymer was dissolved in trichlorethylene and the solution was cast on a lecithin coated glass plate using a standard doctor blade. For 1 mil film, a 10% solution of polymer was cast using a 10 mil setting on the doctor blade. Solvent was allowed to evaporate overnight, and the film was peeled from the plate. The film was dried for at least one week at room temperature before tensile strength was determined. Drying can be accelerated by placing the films in a forced air oven at 60-125° C. Tensile strength date as indicated in the table was obtained according to ASTM D-882.

EXAMPLE 24

21.6 g benzyl alcohol (200 mmoles) in 100 ml toluene was stirred. 5 grams of 5% of tetravalent manganese on carbon catalyst prepared as hereinbefore described (powdered) was added. Oxygen was passed through the vigorously stirred solution for 6 hours at 30° C. The mixture was flushed with nitrogen and filtered. GLC analysis indicated benzaldehyde was an oxidation product.

EXAMPLE 25

N-Phenylhydroxyamine was prepared by treating nitrobenzene with $NH_4Cl$ and zinc dust in water at 0° C. by the method described in Org. Syn. Coll. Vol III, E. C. Horning, Jr., Ed., John Wiley & Sons, Inc., New York, 1955, P. 668. An aliquot of the cold solution containing about 10.9 grams of N-phenylhydroxylamine (100 mmole) was stirred with 5 grams of 5% tetravalent manganese on carbon catalyst at 0°-5° C. under oxygen for 6 hours. The reaction mixture was filtered to remove catalyst. GLC analysis indicated that nitrosobenzene was present. The nitrosobenzene can be recovered by steam distillation. The purified nitrosobenzene melts at 64°-66° C.

What is claimed is:

1. A heterogeneous oxidation catalyst consisting essentially of about 1 to 10% by weight of tetravalent manganese precipitated on porous carbon which is substantially free of mineral impurities.

2. A catalyst as claimed in claim 1 wherein the porous carbon has a surface area of at least 500 $m^2$/grams.

3. A method of preparing a catalyst as claimed in claim 1 which comprises slurry a aqueous solution of a permanganate salt with a porous carbon substantially free of mineral impurities and subsequent thereto drying the slurry at temperatures of below 25° C. to obtain a solid catalyst.

4. A method as claimed in claim 3 wherein the permanganate salt is an alkali permanganate salt.

5. A method as claimed in claim 4 wherein the permanganate salt is potassium permanganate.

6. A method as claimed in claim 3 wherein the drying is accomplished by vacuum drying.

7. A method as claimed in claim 3 wherein the drying is accomplished by freeze drying.

TABLE

| Ex. | Catalyst Amt. | Method (D) | Other | Mix Order | Mole % to Conv. to Low MW | Med. MW | High MW | GPC Mn Med. MW | GPC Mn High MW | Cast Films Tensile Strength High MW |
|---|---|---|---|---|---|---|---|---|---|---|
| 9 | 5 | 1 | Ethanolamine | (A) | 9.5 | 35.8 | 21.6 | — | — | |
| 10 | " | " | TMEDA (G) | " | 8 | 54.6 | 4 | 10,000 | — | |
| 11 | " | " | " | " | 9.2 | 22 | 46 | — | 21,400 | 7,100 |
| 12 | " | " | Pyridine | " | " | 5 | 38(a) (H) 41.6(b) | — | (a)9,680 (b)44,500 | (a)6,700 (b)7,700 |
| 13 | " | " | None | (B) | 15.8 | 54.2 | 0 | — | — | |
| 14 | " | " | Pyridine | (A) | 6.3 | — | (a)25.8 (b)35.0 | — | (a)19,200 (b)21,800 | |
| 15 | " | " | " (F) | (C) | 5.8 | — | (a)27.6 (b)46 | — | (a)20,000 (b)39,400 | |
| 16 | 1.25 | 4 | " | (C) | 35.8 | 0 | 7 | — | — | |
| 17 | 2.5 | 1 | " | " | 20.6 | — | 17 | — | — | |
| 18 | 2.5 | 6 | " | (A) | — | — | (a)16.6 (b)64 | — | (a)16,500 (b)33,900 | |
| 19 | 2.5 | 7 | " | " | 5 | — | (a)28.8 (b)51.4 | — | (a)13,600 (b)22,900 | |
| 20 | 2.5 | " | " (F) | (C) | — | — | (a)17.1 (b)59.5 | — | (a)11,711 (b)29,100 | |
| 21 | 2.5 | " | 2-Picoline | (A) | 21 | 0 | 57.6 | — | 7,060 | |
| 22 | 2.5g | 8 | Pyridine | (C) | — | — | (a)52.5 (b)7.1 | — | (a)11,600 (b)18,700 | |
| 23 | " | " | " | " | — | — | (a)42 (b)41.6 | — | (a)20,400 (b)38,600 | 7,400 |

A. Toluene and amine stirred, KOH added, then 2,6-xylenol added under $N_2$. Stirred ¼ hour under $N_2$. Catalyst added, rinsed in with toluene. Stirred ¼ hour, $N_2$. Stirrer off, flush with oxygen for ¼ hour, 25°. Then on stirrer.
B. Same as (A), except amine omitted.
C. Toluene and KOH stirred, 2,6-xylenol added. Stirred ¼ hour, $N_2$. Catalyst stirred in 10 toluene, amine added, stirred occasionally for ¼ hour. Catalyst-amine slurry added to toluene-KOH-2,6-xylenol. Stirred ¼ hour, $N_2$. Then stirrer off, flushed with $O_2$ ¼ hour, 25°. Then on stirrer.
D. Method indicates that the catalyst was prepared by the numbered example.
F. Pyridine pre-mixed with catalyst in toluene instead of adding amine to toluene-KOH-2,6-xylenol as in previous runs.
G. TMEDA - Tetramethylethylene diamine.
H. (a) indicates fraction extracted by toluene and precipitated into acetone. (b) indicates higher MW fraction extracted by methylene chloride and precipitated into acetone.